US011471331B2

(12) United States Patent
Dittrich et al.

(10) Patent No.: US 11,471,331 B2
(45) Date of Patent: Oct. 18, 2022

(54) EARPLUG FOR SELECTIVE ATTENUATION OF SOUND AND AN INSERT WITH AN ACOUSTIC FILTER FOR USE IN AN EARPLUG

(71) Applicant: EAR LABS AB, Malmo (SE)

(72) Inventors: Christian Dittrich, Loderup (SE); Jason McIntosh, Pensacola, FL (US); Marco Mietta, Appiano Gentile (IT)

(73) Assignee: EAR LABS AB

( * ) Notice: Subject to any disclaimer, the term of this patent is extended or adjusted under 35 U.S.C. 154(b) by 0 days.

(21) Appl. No.: 16/960,174

(22) PCT Filed: Mar. 25, 2019

(86) PCT No.: PCT/SE2019/050266
§ 371 (c)(1),
(2) Date: Jul. 6, 2020

(87) PCT Pub. No.: WO2019/194722
PCT Pub. Date: Oct. 10, 2019

(65) Prior Publication Data
US 2021/0052429 A1 Feb. 25, 2021

(30) Foreign Application Priority Data
Apr. 4, 2018 (SE) .................................. 1800065-3

(51) Int. Cl.
*A47L 9/16* (2006.01)
*A61F 11/08* (2006.01)

(52) U.S. Cl.
CPC ............. *A61F 11/08* (2013.01); *A61F 11/085* (2022.01)

(58) Field of Classification Search
CPC .. H04R 1/1083; H04R 1/2876; H04R 1/1016; H04R 1/105; H04R 1/1041; H04R 25/60;
(Continued)

(56) References Cited

U.S. PATENT DOCUMENTS 5,332,871 A 7/1994 Carrigan
6,082,485 A 7/2000 Smith
(Continued)

FOREIGN PATENT DOCUMENTS

AU 5606773 A 11/1974
EP 1629802 3/2006
(Continued)

OTHER PUBLICATIONS

Bartholdi et al. (Filter Media Performance and Its Influence on Filtration Results-Experience, Expectations and Possibilities in Vacuum and Pressure Filtration, Sefar.com, FILTECH 2015-L13-Filter Media, Feb. 24-26, 2015—Cologne—Germany) (Year: 2015).*
(Continued)

*Primary Examiner* — Alireza Nia
*Assistant Examiner* — Michael Milo
(74) *Attorney, Agent, or Firm* — Tucker Ellis LLP (57) ABSTRACT

An earplug (10, 80) for selective attenuation of sound has a body with at least one sound path. An insert (34) is housed in the body (13), which has at least one sound passage with an acoustic filter. The acoustic filter is configured to provide a specific frequency response and thus a determined attenuation of sound passing through the earplug. Means (14) is arranged at a top surface adapted to activate or deactivate the sound path. Each acoustic filter comprises an upper acoustic port (36, 37), at least one acoustic mesh (35) and/or acoustic membrane (37, 39), an acoustic chamber (41, 44) and a lower acoustic port (42, 43). An insert (34) with an acoustic filter for selective attenuation of sound is provided for use in an earplug.

16 Claims, 10 Drawing Sheets

(58) Field of Classification Search
CPC .......................... H04R 25/652; H04R 25/658; H04R 2460/11; A61F 11/08; A61F 11/10; A61F 11/12; A61F 11/006; A61F 2011/085
USPC .......................... 128/864, 865, 867; 181/135
See application file for complete search history.

(56) References Cited

U.S. PATENT DOCUMENTS

| | | | |
|---|---|---|---|
| 6,148,821 A | 11/2000 | Falco | |
| 7,740,104 B1 | 6/2010 | Parkins et al. | |
| 8,903,114 B2 | 12/2014 | Voix et al. | |
| 9,333,116 B2 | 5/2016 | Bauman et al. | |
| 2003/0159878 A1 | 8/2003 | Hakansson et al. | |
| 2003/0196850 A1* | 10/2003 | Dyer ...................... | A61F 11/08 181/135 |
| 2006/0042865 A1* | 3/2006 | Berg ..................... | H04R 25/658 181/135 |
| 2006/0042867 A1 | 3/2006 | Haussmann et al. | |
| 2006/0045299 A1 | 3/2006 | Haussmann | |
| 2008/0276945 A1 | 11/2008 | Rosen | |
| 2009/0010475 A1* | 1/2009 | Harper ................. | H04R 1/1033 381/374 |
| 2011/0158421 A1* | 6/2011 | Voix ........................ | A61F 11/08 381/72 |
| 2014/0072161 A1* | 3/2014 | Boyle .................... | H04R 5/033 381/346 |
| 2014/0190493 A1* | 7/2014 | Smith .................... | A61F 11/08 128/867 |
| 2014/0190494 A1 | 7/2014 | Ely | |
| 2014/0270257 A1 | 9/2014 | Bauman et al. | |
| 2016/0022499 A1* | 1/2016 | Brown ................. | G10K 11/002 181/135 |
| 2018/0237967 A1* | 8/2018 | Hossain .............. | B01D 69/127 |
| 2019/0254877 A1* | 8/2019 | De Jong ................. | A61F 11/10 |

FOREIGN PATENT DOCUMENTS

| | | | | |
|---|---|---|---|---|
| SE | 527853 C2 | 6/2006 | | |
| WO | WO-2010063079 A1 * | 6/2010 | ............ | B32B 5/022 |
| WO | 2013080005 A1 | 6/2013 | | |

OTHER PUBLICATIONS

Saati (Saatifil Acoustex Technical Data Sheet, Feb. 5, 2018) (Year: 2018).*

Statement Regarding Prior Disclosures by the Inventor or a Joint Inventor entitled "Summary of revealed product-and technical information during the grace period of dBud utility patent." Christian Dittrich et al. Various dates from Apr.-Nov. 2017. pp. 10.

Supplementary European Search Report. Application No. EP19780813. European Patent Office. Munich, Germany. Date of completion of the search: Nov. 11, 2020. pp. 2.

International Search Report; International application No. PCT/SE2019/050266; Patent Cooperation Treaty; Stockholm, Sweden; Date of the actual completion of the international search May 20, 2019; pp. 6.

Written Opinion of the International Searching Authority; International application No. PCT/SE2019/050266; International Searching Authority; Stockholm, Sweden; Date of completion of this opinion May 20, 2019. pp. 6.

International Search Report; International application No. PCT/SE2019/050266; Patent Cooperation Treaty; Stockholm, Sweden; Date of the actual completion of the international search Feb. 19, 2020; pp. 5.

International Preliminary Reporton Patentability; International application No. PCT/SE2019/050266 Patent Cooperation Treaty; Stockholm, Sweden; Date of the actual completion of the international search Jun. 30, 2020; pp. 5.

* cited by examiner

EARPLUG FOR SELECTIVE ATTENUATION OF SOUND AND AN INSERT WITH AN ACOUSTIC FILTER FOR USE IN AN EARPLUG

TECHNICAL FIELD

The present invention relates to an earplug for selective attenuation of sound from the environment reaching the inner ear of a user, where the earplug comprises a body having at least one sound path with a filter arranged in said sound path.

Also, the invention relates to an insert comprising at least one sound passage with an acoustic filter for use in an earplug for attenuation of sound passing through said earplug.

BACKGROUND OF THE INVENTION

Noise pollution is a global and rapidly growing issue. Consistent elevated sound levels, whether at work or in free time, can cause problems such as hearing impairment, hypertension, ischemic heart disease, annoyance and sleep disturbance. Add constant headphone listening, often at volume levels set to exceed the noise from the surroundings, there is no wonder that people worldwide are at risk of hearing loss. For example, hearing impairment is the third most common health problem in USA, where of all adults in USA suffers from some extent of hearing loss.

There are different demands regarding performance and functionality of an earplug from one person to another depending on their profession, and their interests or hobbies. For example, there are situations where noisy background sound should be filtered out while it still must be possible for people to listen and talk with each other, such as in noisy workplaces where an earplug should be a protecting device but must admit conversation between colleagues. Also, there are situations where high sound levels are preferred to be filtered out with an even attenuation, such as at a music concert where it is desired to listen to the music as played with as little distortion as possible but enjoyed at a reduced volume to avoid hearing loss.

To avoid hearing impairments, numerous types of hearing protectors for noise reduction have been proposed to be used in different fields such as military, industrial applications and music. One of the most common hearing protectors is a foam earplug. Foam earplugs are compressed and inserted into the ear canal. When the compression is released, the plug expands to fit the inner morphology of the ear. One of the limitations of foam earplugs is that they block out sound in an uneven way, resulting in unclear and muffled hearing.

U.S. Pat. No. 8,903,114 describes an in-ear device that comprises a main body for placement in the outer ear of a wearer and has at least two derivative canals, each containing a filter medium differing from one another in terms of their frequency suppression capabilities, where a rotatable knob is provided to enable selection of canal.

U.S. Pat. No. 6,148,821 discloses a selective nonlinear attenuating ear protection plug. The earplug is tunable by the wearer and permits to select between a selective attenuation mode and a maximum attenuation mode, in which the hearing protector claims to stop all sounds throughout the frequency range regardless their intensity.

SE 527 853 and US20030159878 relates to an earplug with a through duct, in which a membrane element is arranged comprising a membrane and a holder for said membrane. Said membrane is made of silicone, which makes it completely airtight and results in that an uncomfortable sensation of vacuum is created within the ear canal.

U.S. Pat. No. 6,082,485 presents an earplug with a rotationally adjustable gating mechanism for adjustable attenuation of treble sounds. The ear plug includes a conventional earplug foam body that has a partial aperture axially of the earplug and a two-part counter rotating gating member that fits to said aperture. Upon relative rotation of said parts of the member different sound apertures rotates in and out of registry of said gate for selectively attenuating treble sounds.

U.S. Pat. No. 9,333,116 describes a sound attenuator that allows a user to adjust the amount of attenuation in a variable, continuous fashion or in a discrete controlled fashion from zero attenuation to maximum attenuation without removing the device from the ear. The ear attenuator includes a housing with a passageway, which allows sound to pass through the housing, and a variable control that enables to control the size of the passageway through the housing and the amount of attenuating material located within the passageway.

Currently available ear plugs on the market are generally designed to block as much sound as possible from the environment thereby protecting the ears of the wearer. These earplugs often block some frequencies more than others resulting in that the hearing protection is not uniform for all frequencies. Existing earplugs have limitations regarding functionality and performance, such as a large spread in attenuation, resulting in distorted and muffled hearing.

Accordingly, there is a need for an improved ear plug that enables the wearer to switch between different levels of attenuation for hearing protection, without compromising on voice communication and sound experience, which would be advantageous at various use, both professionally and in recreational situations.

SUMMARY OF THE INVENTION

An object of the present invention is to mitigate or eliminate one or more deficiencies and disadvantages of the prior art, such as the above-identified, singly or in any combination, by providing an ear plug according to the appended patent claims.

In a first aspect the invention relates to an ear plug for selective attenuation of sound from the environment reaching the inner ear of a user.

The earplug according to a first embodiment comprises a body having at least two sound paths extending from a top surface with at least two inlets facing the ambient air and through said body. The body comprises an insert having at least two sound passages, where an acoustic filter is arranged in each of said at least two sound passages. Each acoustic filter comprises an upper acoustic port, at least one acoustic mesh and/or at least one acoustic membrane, an acoustic chamber and a lower acoustic port.

A specific attenuation of sound passing each filter is determined by a combination of a selected size of an open area of said upper and lower acoustic ports, a selected size of an open surface area of said at least one acoustic membrane and/or said at least one acoustic mesh, and a selected air permeability of said at least one acoustic membrane and/or said at least one acoustic mesh.

Means is arranged at said top surface configured to activate or deactivate the at least two sound passages and to close a sound passage not in use. Said means is for example a member configured to slide between selected positions according to a preferred embodiment.

The body comprises an upper body with the top surface comprising a side wall protruding from the top surface. Inward facing rims are arranged at the side wall for engagement with recesses of the member for holding it while enabling it to slide between said positions. Further, the body comprises a lower body comprising a first portion of a diverging cone shape for housing said insert and a second portion with a tubular end adapted to be inserted into the ear canal.

The insert according to the first embodiment comprises a first sound passage with a first acoustic filter having a first upper acoustic port, a first acoustic mesh, a first acoustic chamber and a first lower acoustic port and comprises a second sound passage with a second acoustic filter having a second upper acoustic port, a second acoustic mesh, a first acoustic membrane, a second acoustic chamber, a second acoustic membrane and a second lower acoustic port. Said two sound paths, respectively, are extending from inlets at the top surface of the upper body and through the acoustic filters to an outermost end of the tubular portion of the lower body.

The earplug according to a second embodiment comprises a body having at least one sound path configured to extend from a top surface with at least one inlet facing the ambient air and through said body. An acoustic filter is arranged in said at least one sound path, which comprises an upper acoustic port, at least one acoustic mesh and/or at least one acoustic membrane, an acoustic chamber and a lower acoustic port.

Each of said acoustic filters of the first and second embodiment will provide a unique frequency response and hence attenuation of sound from the ambient air passing through the sound paths and reaching the inner air of the wearer of the ear plug.

The first embodiment of the ear plug comprises a low attenuation sound path configured to pass the human voice clearly while disturbing background noise is reduced, and a high attenuation path configured to provide an even attenuation with low distortion for all frequencies.

A specific frequency response and hence attenuation of sound passing each of said filters is determined by a combination of a selected size of an open area of said upper and lower acoustic ports, a selected size of an open surface area of said at least one acoustic membrane and/or said at least one acoustic mesh and a selected air permeability of said at least one acoustic membrane and/or said at least one acoustic mesh. The member arranged at the top surface is configured to slide between selected positions to activate or deactivate one of the at least two sound passages and hence to close sound paths not in use.

There are five parameters for determination of a specific frequency response of each acoustic filter and hence the attenuation. The first parameter is a stiffness of said acoustic membranes and said acoustic meshes, which is controlled by changing an open surface area of said acoustic membranes and said acoustic meshes. The second parameter is a DC flow resistance of said acoustic membranes and said acoustic meshes, which is controlled by changing an open surface area and said air permeability, respectively, of said acoustic membranes and said acoustic meshes. The third parameter is a surface weight, a thickness and/or said open surface area of said acoustic membranes and said acoustic meshes. The fourth parameter is a volume and shape of said acoustic chambers. The fifth parameter is an open area of said acoustic ports.

According to the first embodiment of the earplug, the first acoustic filter is configured to provide an average attenuation of about −15 dB and the second acoustic filter is configured to provide an average attenuation of about −30 dB.

In the ear plug according to the second embodiment, the acoustic filter could be configured to provide selected attenuations due to the parameters related to the stiffness and DC flow resistance of said acoustic mesh and membrane, which is controlled by changing the open area of said mesh and membrane, and by choosing a specific weight, thickness and open area of said mesh and membrane. For example, the attenuation could be −15 dB or −30 dB.

An alternative second embodiment of the ear plug comprises an insert arranged in said body having at least one sound path where said acoustic filter is arranged.

In a second aspect of the invention an insert is provided for use in an earplug for selective attenuation of sound. Said insert comprises at least one sound passage having an acoustic filter arranged therein.

Further objects, features and advantages of the present invention will appear from the following detailed description, the attached drawings and the appended claims.

BRIEF DESCRIPTION OF THE DRAWINGS

In order to explain the invention, embodiments of the invention will be described below with reference to the drawings, in which.

Same reference numerals have been used to indicate the same parts in the figures to increase the readability of the description and for the sake of clarity.

DESCRIPTION OF EMBODIMENTS OF THE INVENTION

Specific embodiments of the invention will now be described with reference to the accompanying drawings.

This invention may be embodied in many different forms and should not be construed as limited to the embodiments set forth herein; these embodiments are provided so that this disclosure will be thorough and complete, and will fully convey the scope of the invention for those skilled in the art. The terminology used in the detailed description of the embodiments illustrated in the accompanying drawings is not intended to be limiting of the invention.

The earplug 10 according to a first embodiment of the invention is configured to provide selective attenuation of frequencies of sound from the ambient air reaching the inner ear of a user. The earplug has at least two sound paths extending through a body, where an acoustic filter is arranged in each of said at least two sound paths. Said acoustic filter is configured to provide a predetermined attenuation of selected frequencies.

A preferred first embodiment of the earplug has two sound paths configured to extend from a top surface 12 of the body through the body and will reach the inner ear of a user at an outermost end of a tubular portion 13B of the body. The tubular portion 13B is adapted for insertion into the ear canal. The earplug provides a low attenuation mode and a high attenuation mode due to determined parameters of the acoustic filters. By means 14 arranged at a top surface 12, the user can switch from a first mode to a second mode without removing the earplug from the ear. Said means 14 is for example a sliding member.

The low attenuation mode reduces background noise while maintaining a clear hearing of human speech (70-400 Hz) in noisy environments, which allows the user to hear and communicate more clearly compared to prior art earplugs and compared to not using any earplugs, while the ears are protected.

The high attenuation mode provides an even frequency response across the entire frequency range resulting in a low acoustic distortion and thereby a clearer listening experience compared to prior art earplugs, for example at music concerts and other events providing high sound levels. The even frequency response of the high attenuation mode also ensures a uniform protection across the entire frequency range, whereas most prior art earplugs only provide various degrees of protection at different frequencies.

Figure 1:
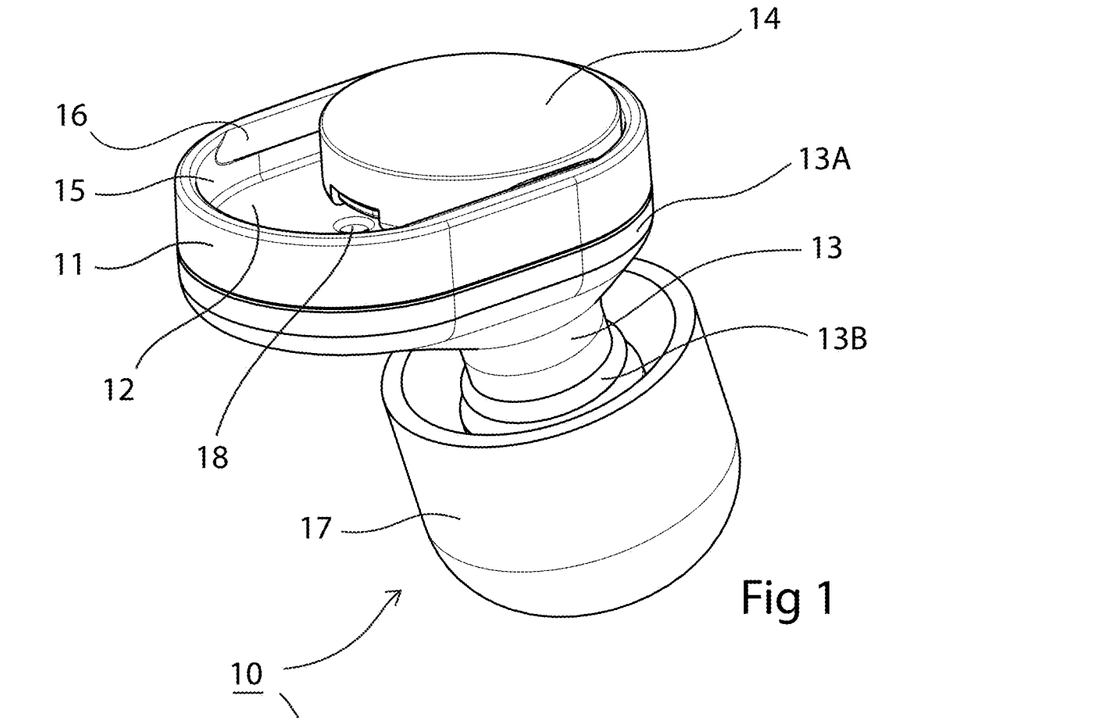
FIG. 1 is a perspective back view of an earplug according to the invention.

FIG. 1 shows a perspective back view of the earplug 10 according to the first embodiment. The ear plug comprises an upper body 11 having a top surface 12, a lower body 13 and a substantial circular member 14 configured to slide between a first and a second position for covering and hence closing one of the sound paths that is not activated, which will be described in further detail below.

Figure 3:
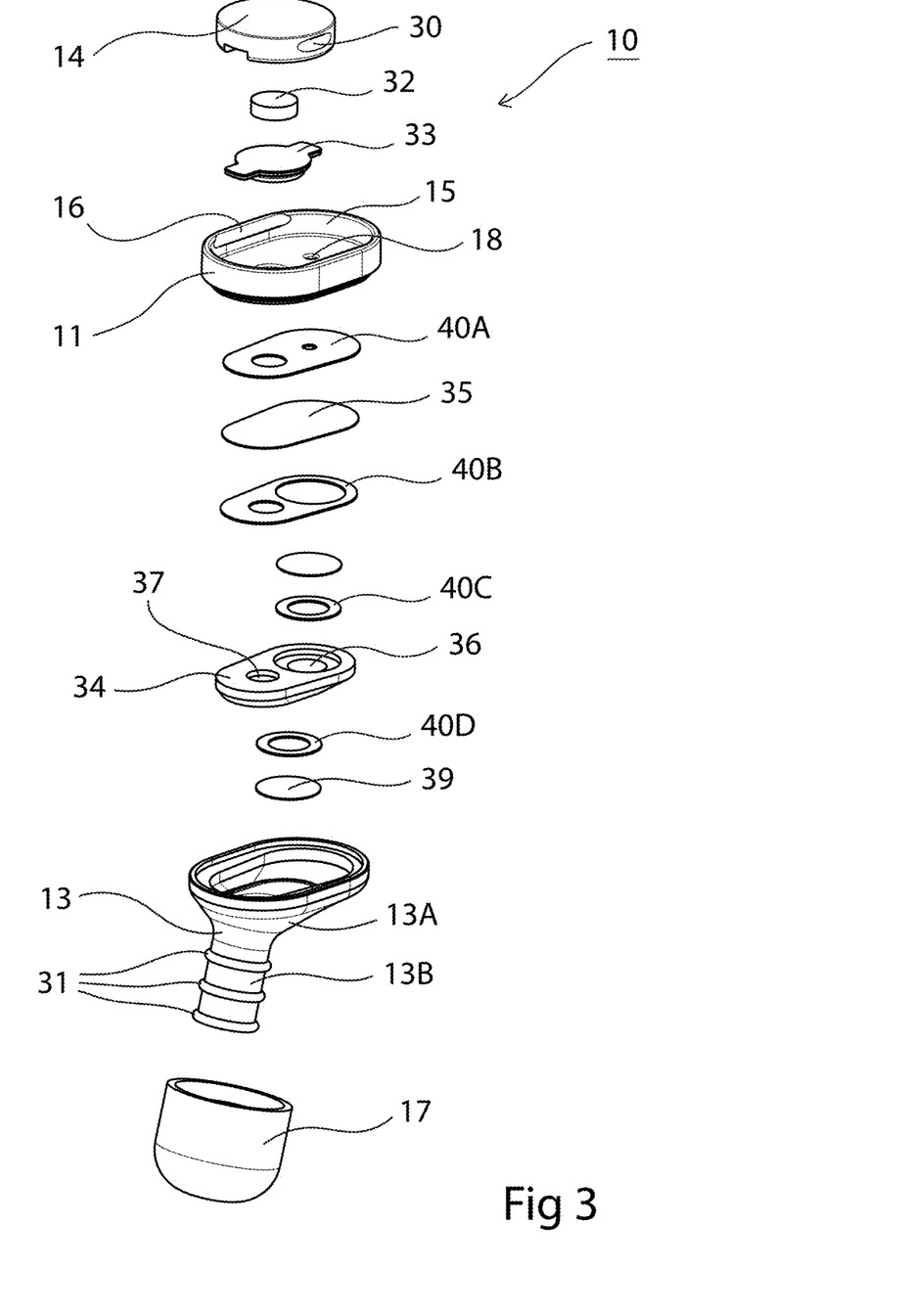
FIG. 3 is an exploded perspective front view of the earplug in FIG. 1.
Figure 5:
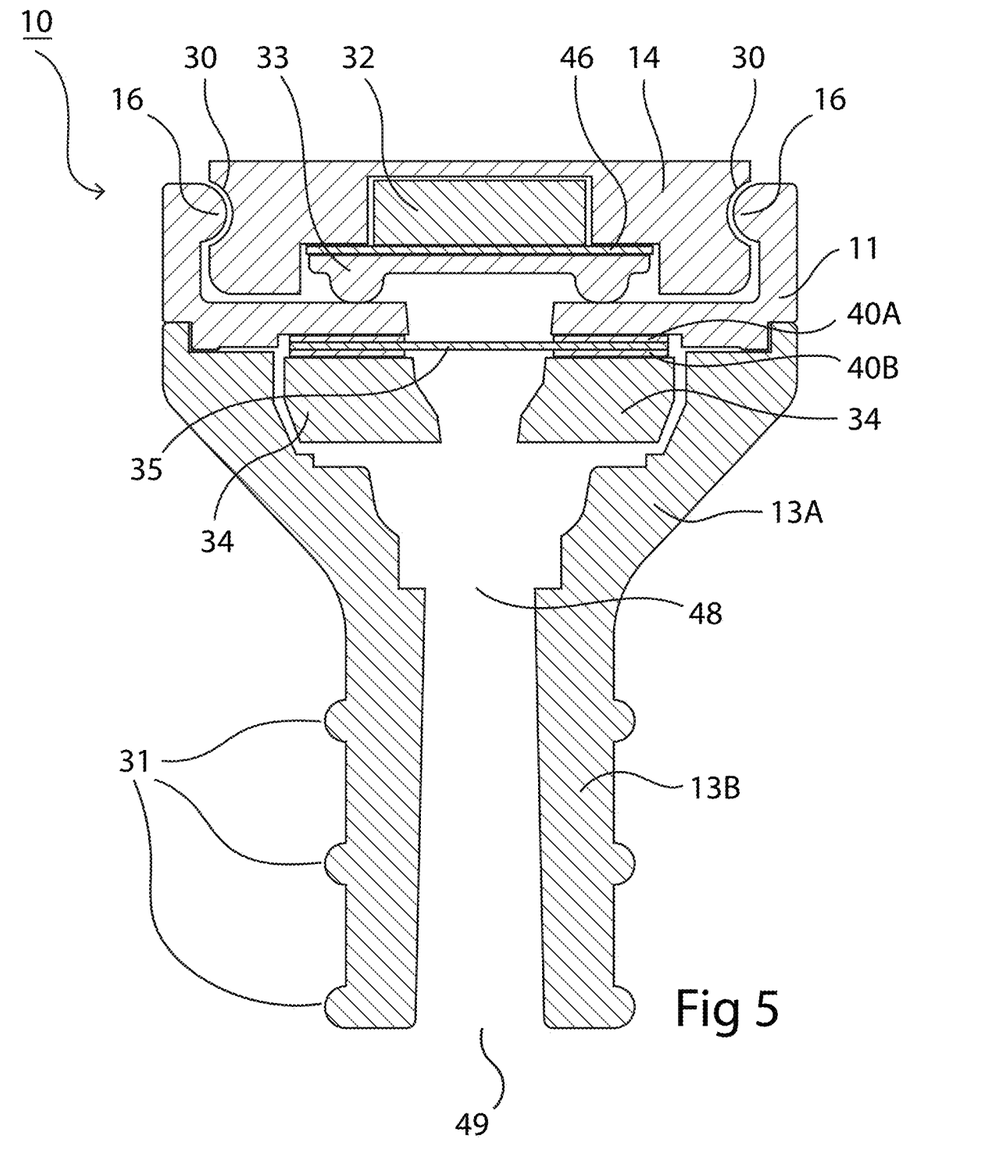
FIG. 5 is a cross-sectional front view of the ear plug without a tip arranged to the lower body, showing a sliding member arranged in engagement with rims at an upper body.

The upper body 11 has a track race shape and has a circumferential side wall 15 protruding upward from the top surface 12, where inward facing rims 16 are arranged at long sides of said wall 15, which rims are adapted for engagement with recesses 30 of the member 14 (see FIG. 3 and FIG. 5). The rims 16 and the recesses 30 in engagement with each other are configured for holding the member 14 while enabling it to slide between said determined positions.

The lower body 13 has a first portion 13A of a diverging cone shape and a second portion 13B of a tubular shape for insertion into the ear canal of the user. A tip 17 having a through bore is removably arranged around the second portion 13B for providing an airtight fit in the ear canal. Said tip 17 is made of a resilient material, such as silicone rubber or polyurethane foam, to provide said airtight fit and a comfortable fit for the user.

A second inlet 45 (shown in FIG. 4) and a first inlet 18 of the upper body 13A are opening at the top surface 12 to admit sound from the surroundings into a first and second sound path. Said second inlet 45 is covered by the member 14 in FIG. 1 due to the selected position of the member 14.

Figure 2:
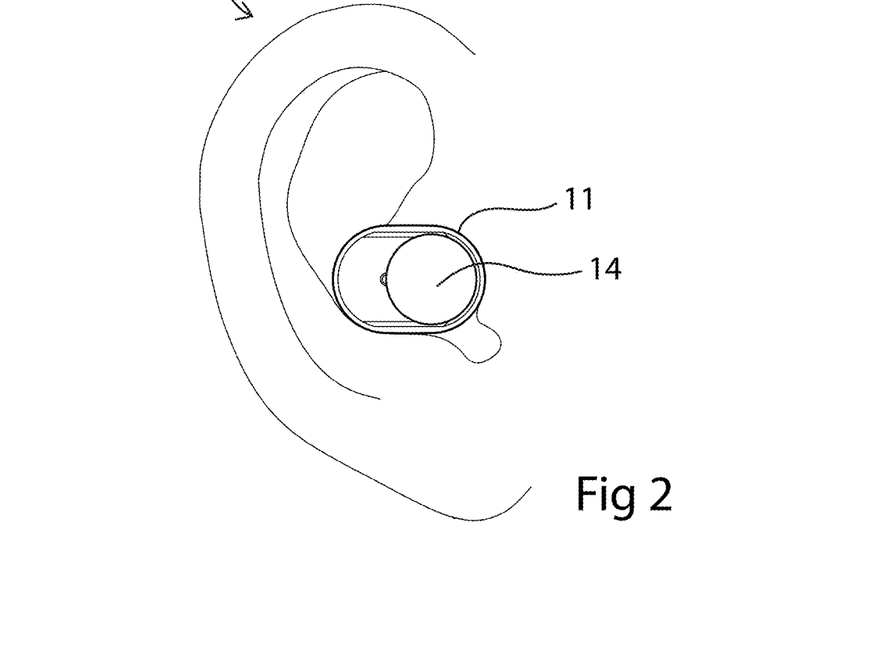
FIG. 2 schematically illustrates the earplug inserted in a right ear of a user.

FIG. 2 schematically illustrates the earplug 10 correctly inserted in a right ear of a user.

FIG. 3 is an exploded perspective front view of the earplug 10 in FIG. 1, without the tip 17, which schematically shows the different components of the earplug according to the first embodiment. The recesses 30 are symmetrical arranged at circumferential sides of said member 14 for engagement with the rims 16 at the side wall 15 of the upper body 11.

The member 14 is configured to house a magnet 32 and a seal 33. The magnet is provided for enabling connection to another earplug of a pair of earplugs and is for example made of neodymium. A leash can be attached to the bodies of the earplugs and due to the magnets of the members it is easy for a user to always wear a pair of earplugs around the neck.

The seal 33 is arranged between the member 14 and the top surface 12 of the upper body 11 for providing an airtight sealing therebetween and to secure that no sound will enter the sound path covered by the member 14.

The earplug 10 according to the first embodiment further comprises an insert 34 having two sound passages, where an acoustic filter is arranged in each of said sound passages. A first upper acoustic port 36 of the first acoustic filter and a second upper acoustic port 37 of the second acoustic filter is arranged at a top side of said insert 34. The insert 34 and said acoustic filters will be described in connection with FIG. 4, FIG. 6 and FIG. 7.

Adhesives 40A, 40B, 40C, 40D are provided to attach the acoustic mesh 35 and the acoustic membranes 38, 39 to the insert 34, and are adapted in size to leave the sound passages free from adhesives and to provide an airtight sealing between said components.

The lower body 13 comprises the first portion 13A of a diverging funneled shape for housing said insert, and the second portion 13B adapted to be inserted into the ear canal. Ribs 31 are arranged surrounding the second portion 13B to ensure that the tip 17 will stay attached to said second portion 13B. The ribs 31 are arranged at a distance from each other, due to the dimensions of the ear plug, the number of ribs are two to five, preferably three. According to an alternative embodiment, the ribs are omitted, and the tip is arranged to the tubular portion by press passing.

Figure 4:
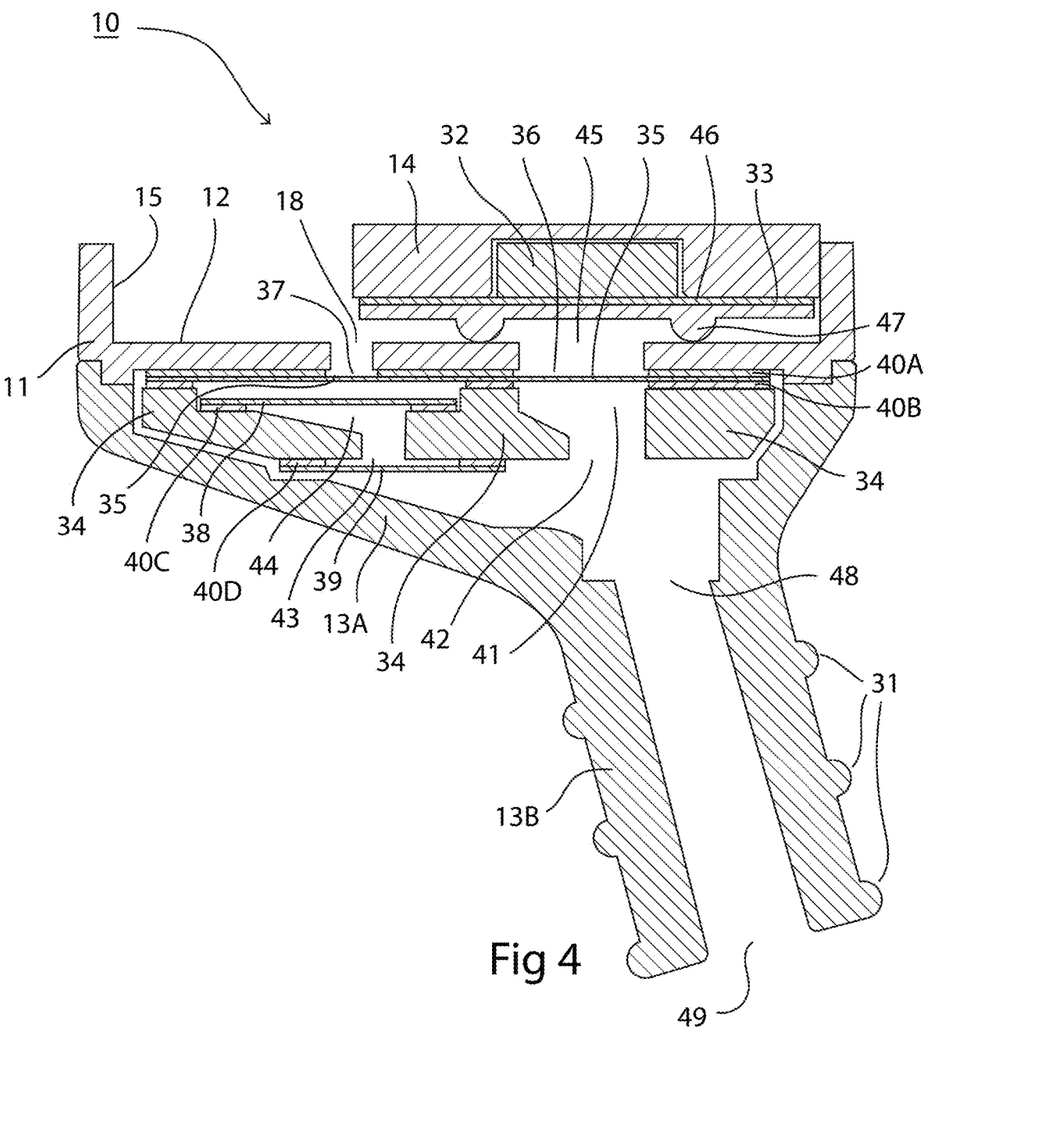
FIG. 4 is a cross-sectional side view of the earplug without a tip arranged to a lower body, showing an insert arranged within an upper portion of said lower body.

FIG. 4 shows the earplug 10 in cross section according to the first embodiment, illustrating the upper body 11 with the member 14 arranged thereto and the lower body 13 housing the insert 34.

The first inlet 18 and the second inlet 45 are arranged at the top surface 12 of the upper body 11 for admitting sound from the surroundings to enter the sound paths elongating through the earplug and to reach the inner ear of the user.

The member 14 is configured to slide between the first and second position to cover one of the inlets 18, 45 of the top surface 12 for activating a selected sound path.

The sound path not selected for use will be covered by the sliding member 14. The seal 33, housed in the member 14 and arranged in abutment with the top surface 12 of the upper body 11, ensures that an airtight sealing is achieved therebetween and secures that no sound will enter the inlets 18, 45 when the member 14 covers one of these, hence blocking sound to enter the corresponding sound path. The seal 33 has protrusions 47 that are compressed when the recesses 30 of the member 14 are in engagement with the ribs 16, which will further contribute to achieve the airtight sealing.

The member 14 is made of a solid material, such as stainless steel, a dense polymeric material or other material of high density to block any sound through the member 14.

The upper portion 13A of the lower body 13 is configured to house the insert 34. Said insert 34 has a first sound passage comprising a first acoustic filter, and a second sound passage comprising a second acoustic filter. According to the first embodiment, said first acoustic filter comprises the first upper acoustic port 36, a first acoustic mesh 35, a first acoustic chamber 41 and a first lower acoustic port 42. Said second acoustic filter comprises the second upper acoustic port 37, an acoustic mesh 35, a first acoustic membrane 38, a second acoustic chamber 44, a second lower acoustic port 43 and a second acoustic membrane 39.

The first and second upper acoustic ports 36, 37 are arranged in alignment with the corresponding inlets 45, 18 of said top surface 12. Said first and second lower acoustic ports 42, 43 are arranged closed to an innermost first end 48 of the second portion 13B of the lower body 13.

The second portion 13B has a through bore extending from the first end 48 adjacent the first portion 13A to a second outermost end 49, where the inner diameter of said second portion 13B is slightly larger at the outermost second end than the diameter at the first end thereby forming a slightly conical channel.

FIG. 5 shows the earplug 10 without the tip 17 in a cross-sectional front view, illustrating that the recesses 30 are symmetrical arranged at the circumferential sides of the member 14 for engagement with the ribs 16, which are arranged at the protruding side wall 15 of the upper body 11.

Figure 6:
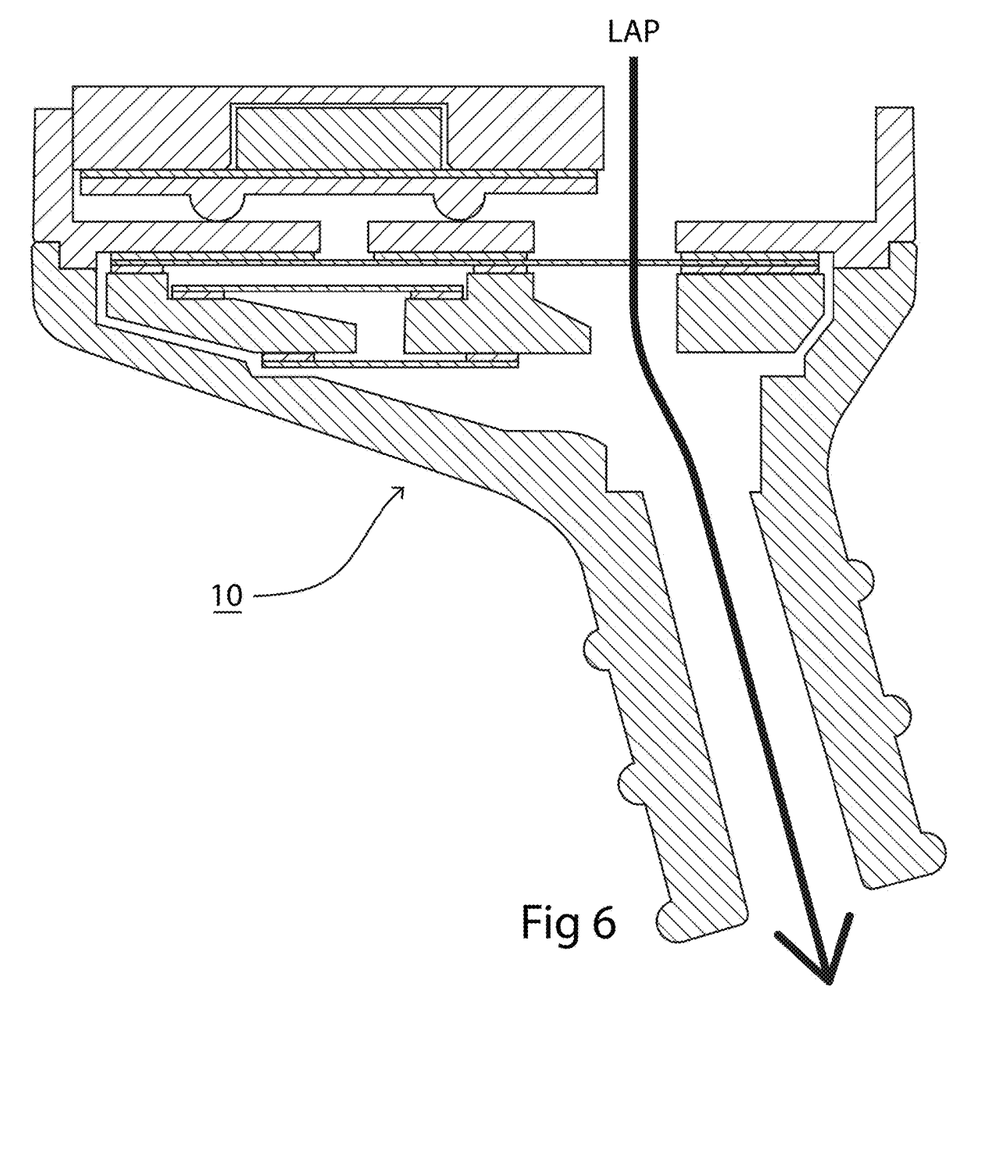
FIG. 6 is a cross sectional side view of the ear plug, showing a low attenuation sound path through the ear plug.

FIG. 6 illustrates a low attenuation mode of the ear plug 10, wherein the member 14 is arranged in the first position, resulting in that the inlet 18 is covered and the inlet 45 is open thus admitting sound to enter the low attenuation sound path, as illustrated by the arrow LAP.

Sound from the environments enters the earplug 10 through the first inlet 45 at the top surface 12 and passes through the first upper acoustic port 36, the acoustic mesh 35, the first acoustic chamber 41, the first lower acoustic port 42 and then leaves the first sound passage of the insert 34 for passing through the second portion of the lower body 13B to the inner ear of the user.

Figure 7:
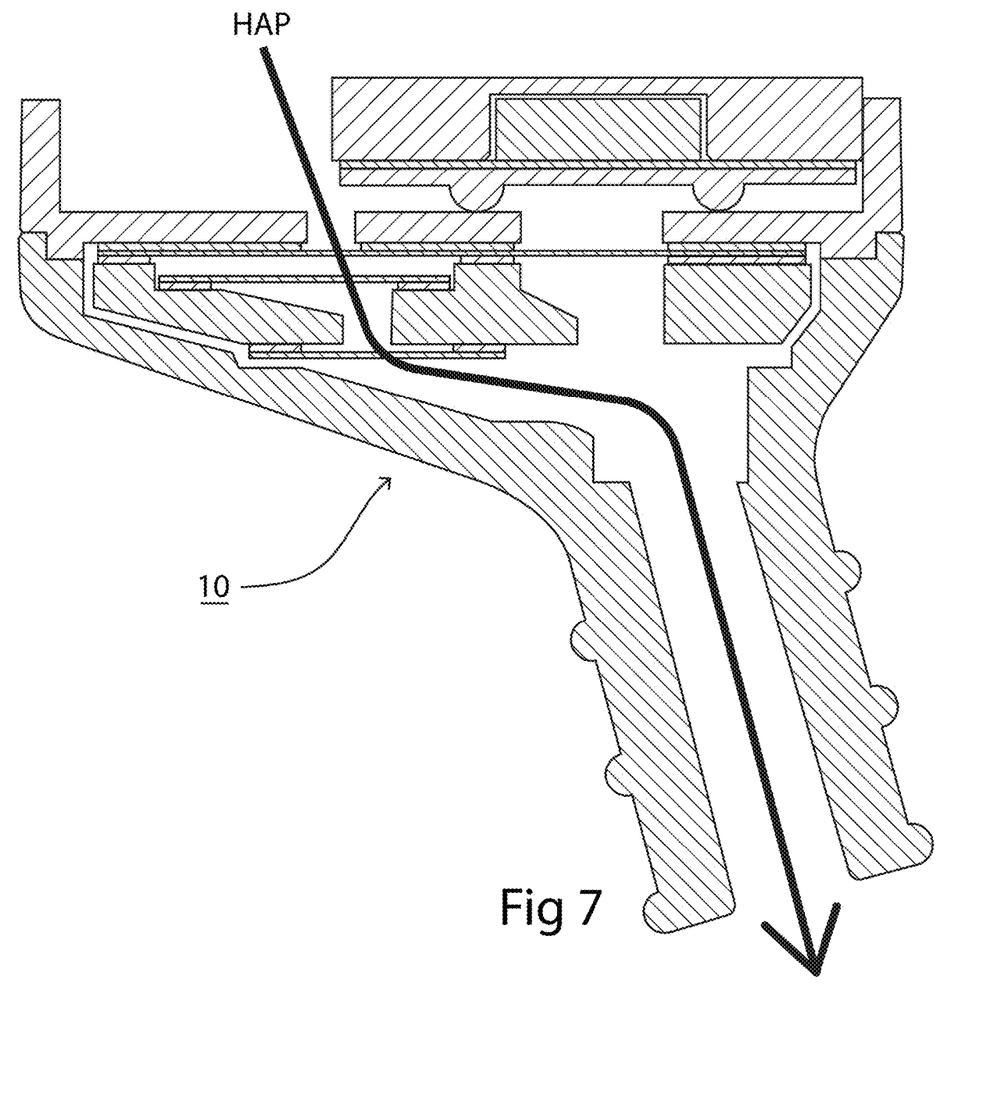
FIG. 7 is a cross sectional side view of the ear plug, showing a high attenuation sound path through the ear plug.

FIG. 7 illustrates a high attenuation mode of the earplug 10 which is activated by sliding the member 14 to the second position. In the high attenuation mode, the inlet 45 is covered and the inlet 18 is open, thereby sound is admitted entrance to the high attenuation sound path of the earplug 10, as illustrated by the arrow HAP. The sound enters the second inlet 18 and then passes through the second upper acoustic port 37, the acoustic mesh 35, the first acoustic membrane 38, the second acoustic chamber 39, the second lower acoustic port 43 and the second acoustic membrane 44 and leaves the second sound passage of the insert 34 for passing through the second portion 13B of the lower body 13 to the inner ear of the user.

The seal 33 efficiently secures that an airtight sealing is provided between the sliding member 14 and the top surface 12 of the upper body 11 for covering the inlet of the sound passage not in use, which is essential to achieve a determined level of attenuation.

Another feature of the seal 33 is the contribution thereof regarding a smooth and easy sliding function of the member 14 to enable the user to switch from the first mode to the second without removing the earplug from the ear.

Various materials have been tested for optimizing the design of the seal, including materials such as Poron foam gaskets, low friction Teflon tapes, nitrile rubber O-rings as well as silicone rubber gaskets. A custom-made silicone rubber gasket proved to be superior as material of the seal 33 compared to other types of material. The final design of the seal 33 comprises a custom made substantial circular silicone seal having a hardness of about Shore 45 A and a nominal pre-compression of 0.3 mm.

Figure 8:
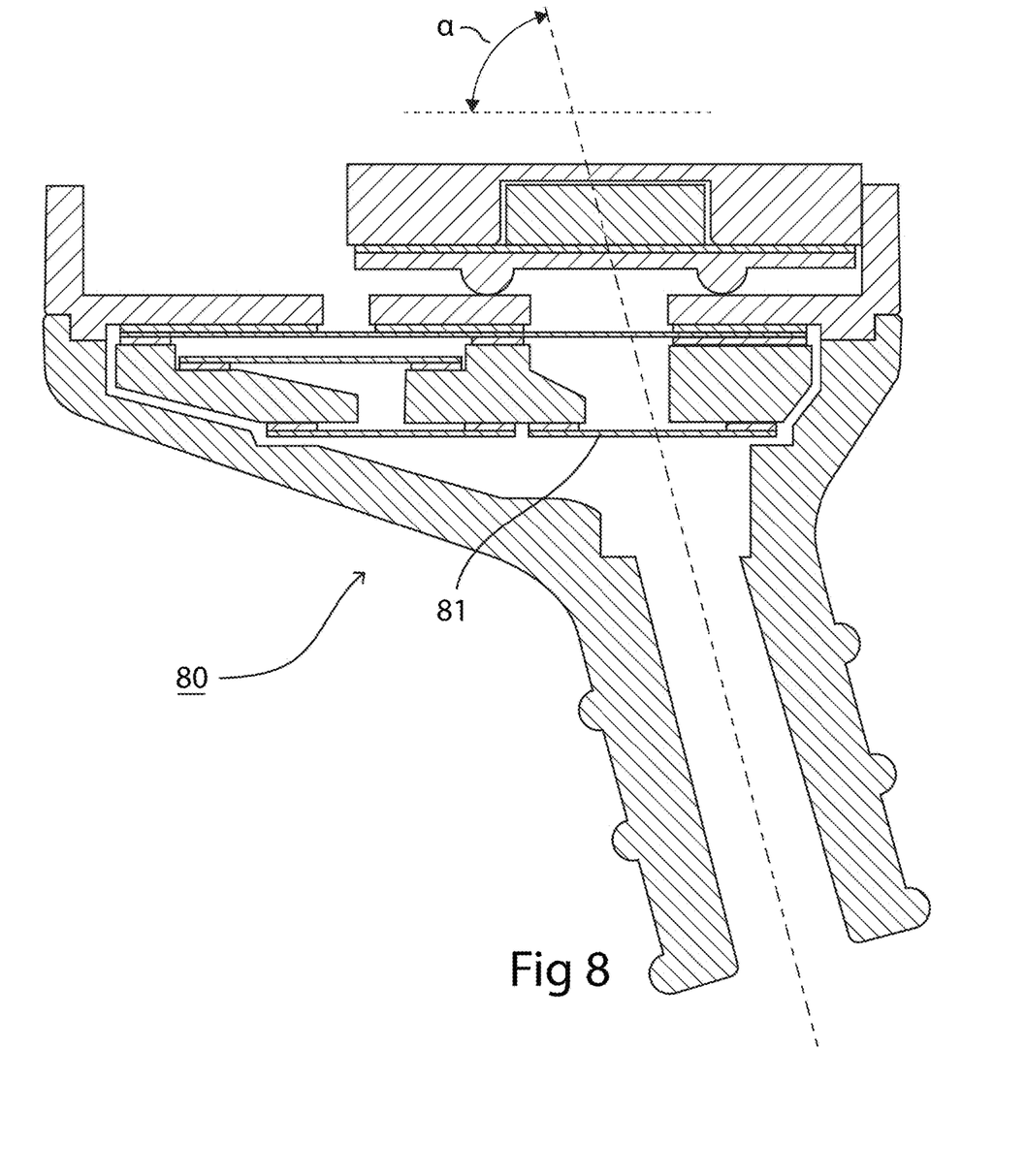
FIG. 8 is a cross sectional side view, showing the earplug according to a second embodiment having an additional acoustic membrane.

FIG. 8 shows an earplug 80 according to an alternative embodiment, wherein said first acoustic filter further comprises a third acoustic membrane 81, while the second acoustic filter is identical with the second one according to the first embodiment of the earplug 10. Due to said third acoustic membrane 81, the attenuation of sound passing through the first sound passage of the ear plug 80 will be different from the attenuation of sound passing the first sound passage of the first embodiment of the ear plug 10.

The earplug according to a second embodiment comprises a body having one sound path configured to extend from a top surface with one inlet facing the ambient air and through said body. An acoustic filter is arranged in said sound path, which comprises an upper acoustic port, at least one acoustic mesh and/or at least one acoustic membrane, an acoustic chamber and a lower acoustic port. It should be understood that the second embodiment has the same main parts as the ear plug according to the first embodiment, the difference is that only one sound path is provided and hence the inner of the body is configured to provide only one sound path. It is not necessary to provide means to activate or deactivate the sound path of the ear plug according to the first embodiment.

An alternative first or second embodiment could be constructed without the separate insert 34 due to chosen manufacturing method. Then, the acoustic membranes and meshes are arranged to inner areas of the body and said inner areas are configured to form upper and lower acoustic ports, and the acoustic chamber. For example, if moulding is used for production, either in a one shot or multi shot process, the insert could be made integral with the body.

FIG. 8 shows that the second portion of the lower body 13B is arranged in an angle $\alpha$ to a horizontal plane in parallel with the top surface 12 of the upper body 11, wherein said angle $\alpha$ is about 10 to 20 degrees, and preferably about 15 degrees for adaption to the ear canal of a user.

The acoustic membranes are made of a polymeric material, such as PTFE, and are configured as a thin porous film with an air permeability within the range of 4-150 $L/m^2$ s at a pressure of 200 Pa and with a DC flow resistance within the range of 2500-40 000 MKS Rayls.

The acoustic meshes are made of a polymeric material, such as polyester, and are configured as a woven mesh of monofilaments of said polymeric material with an air permeability within the range of 250-2500 L/m2s at a pressure of 200 Pa and a DC flow resistance within the range of 100-800 MKS Rayls.

The air permeability and the stiffness of the acoustic mesh and membranes are essential features of the inventive earplug, and further the combination of meshes and membranes of different air permeability and stiffnesses for providing a determined attenuation and frequency response of each acoustic filter.

The meshes 35 of the acoustic filters of the first embodiment 10 and the second embodiment 80 of the ear plug are identical, however these can differ from each other and/or an additional mesh 35 or membranes having different features can be provided in alternative embodiments to achieve other predetermined frequency responses and attenuations.

In this context, the open surface area is defined as the open area of the meshes and membranes, respectively, due to the structure thereof. The meshes are made of monofilaments leaving an open area between said monofilaments. The membranes are made of a porous thin film leaving open pores. Said structures are essential to achieve a controlled air permeability through said meshes and membranes.

It shall be noted that prior art earplugs comprising for example a filter made of silicone provides an airtight earplug with no air permeability, which will create a sensation of vacuum in the ear canal leading to an unpleasant feeling for the user and an uncontrollable frequency response.

Each sound path of the earplug according to the invention has a unique acoustic filter providing a predetermined level of attenuation as well as a specific frequency response. In general, the frequency response for each filter, and hence the attenuation in connection with said acoustic filter, is determined by five main control parameters.

The stiffness of said acoustic membranes and said acoustic meshes, respectively, is a first parameter for determination of a specific frequency response of said acoustic filter and hence the attenuation, which is controlled by changing an open surface area of said acoustic membranes and said acoustic meshes.

The DC flow resistance of said acoustic membranes and said acoustic meshes, respectively, is a second parameter for determination of a specific frequency response of said acoustic filter and hence the attenuation, which is controlled by changing the open surface area and said air permeability of said acoustic membranes and said acoustic meshes.

A surface weight, a thickness and/or said open area of said acoustic membranes and said acoustic meshes, respectively, is a third parameter for determination of a specific frequency response of said acoustic filter, and hence the attenuation.

A volume and shape of said acoustic chambers is a fourth parameter for determination of a specific frequency response of said acoustic filter, and hence the attenuation.

An open area of said acoustic ports is a fifth parameter for determination of a specific frequency response of said acoustic filters, and hence the attenuation.

Said parameters has each various impact on the frequency response and hence the attenuation of said acoustic filters. For example, by changing parameter 1 and 2, the frequency response below 2 kHz can be controlled. However, said parameter 1 and 2 are connected to each other since both depend on the open surface area. Also, a small mesh and/or membrane is stiffer than a large one. By changing parameter 3 the frequency response from about 1-3 kHz and above 7 kHz can be controlled. By changing parameter 5 the frequency response from about 3 to 7 kHz can be controlled, however since the earplug has limitations regarding the size to fit in the ear, the parameter 5 has less influence as a control parameter.

The possibility to modify the properties of the acoustic filter, resulting in different frequency responses, will allow configuration of ear plugs adapted for different environments and hence demands from various users.

In general, many of the existing earplugs on the market are designed to block as much as possible of the ambient sound from reaching the middle ear of a user, and certain of these earplugs block some frequencies better than others, resulting in that the hearing protection is not uniform for all frequencies. Other earplugs are designed to reduce only some of the noise, and will let some sound into the ear canal, which is usually accomplished through very small ports with nonlinear behavior to restrict the loudest sounds more than the quiet sounds. However, none of these approaches are good for achieving a uniform reduction of sound for all frequencies, where low frequencies are particularly difficult.

Figure 12:
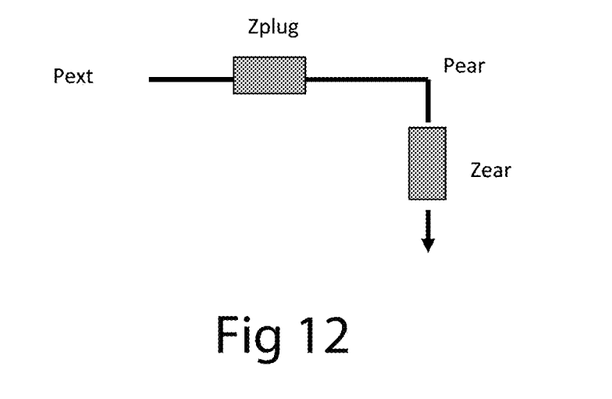
FIG. 12 is a diagram of an earplug and an ear modeled as acoustical impedances.

To compute a determined attenuation, an earplug and the ear can be modeled as acoustical impedances as shown in FIG. 12, where Zplug is the impedance of the ear plug, Zear is the impedance into the ear canal, Pext is the external sound pressure and Pear is the pressure in the ear canal.

Using circuit impedance results in:

$$Pear = Pext * Zear/(Zear + Pplug) = Pext/(Zplug/Zear + 1)$$

To get a uniform reduction of pressure for all frequencies, the ratio Zplug/Zear must be a constant value. However, at low frequencies, generally below approximately 4 kHz, the impedance of the ear Zear is like a closed volume, which has an impedance of:

$$Zear \approx rho * c * c/(iw * Vvol),$$

where rho is the density of air, c is the sound velocity, w is the radian frequency and Vvol is the volume of air in the ear canal.

The impedance of a small hole or port is: Zport=iw*rho*L/S, where L is the length of a port, S is the cross section of an area of a port and i is an imaginary number.

Note that Zear~1/w, while Zport~w, resulting in that Zport/Zear~w^2, which is not a constant value. Thus, a small hole or port is not a good choice to achieve a constant attenuation for all frequencies.

However, the impedance of a membrane is: Zmem=1/(iw*Cmem*Smem^2), where Cmem is the compliance of the membrane and Smem is the surface area of the membrane.

Note that Zmem~1/w, resulting in that Zmem/Zear~K, where K is a constant value equal to:

$$K = (1/(iw * Cmem * Smem\hat{\,}2))/(rho * c * c/(iw * Vvol)) = (Vvol/Cmem)/(Smem\hat{\,}2 * rho * c\hat{\,}2)$$

Hence, if the impedance of the ear plug, Zplug is equal to the impedance of a membrane Zmem, then the ear plug will achieve a constant attenuation for all frequencies, and specifically for those under 4 kHz.

The insertion loss IL in dB is:

$$IL(dB) = 20 * \log 10(Pext/Pear) = 20 * \log 10(Zplug/Zear + 1)$$

where IL is a positive quantity indicating a pressure reduction when insertion of the earplug in the ear canal.

If the impedance of the earplug is equal to the impedance of the membrane:

$$Zplug = Zmem \text{ and } Zmem/Zear = K, \text{then } IL(dB) = 20 * \log 10(K+1)$$

Insertion of K results in:

$$IL(dB) = 20 * \log 10((Vvol/Cmem)/(Smem\hat{\,}2 * rho * c\hat{\,}2) + 1)$$

or $$Cmem = Vvol/(((10\hat{\,}(IL(dB)/20)) - 1) * (Smem\hat{\,}2 * rho * c\hat{\,}2))$$

Given a desired insertion loss IL in dB and a volume of air residing in the ear canal, the desired membrane compliance Cmem can be computed. A typical ear canal has a length of approximately 2.5 cm and a diameter of 7 mm, knowing how far an earplug will protrude into the ear canal, the Vvol of the remaining air in the ear canal can be computed.

The theoretical background above has been utilized to configure the frequency responses and attenuation levels for the inventive earplug. The desired average value of attenuation of sound passing the first acoustic filter, and thus the low attenuation sound path LAP, was determined to −15 dB. The desired average value of attenuation of sound passing the second acoustic filter, and thus the high attenuation sound path HAP, was determined to −30 dB.

Several simulations and acoustic laboratory tests were performed to set the configuration of the earplug 10, 80 for achieving the determined low and high attenuations. By modifying the five control parameters, several iterations were made to find the desired frequency response for each acoustic filter. A functional prototype of the earplug was built for each iteration by using 3D printing technology, including inlets, acoustic ports and acoustic chambers of the body. Laser cutting technology was used for configuration of the acoustic meshes, membranes and adhesives. Then, the actual frequency response for each of the physical prototypes were measured and compared to computed values, thereafter evaluation was made to conclude which of the parameters that should be changed. This process was repeated until a prototype of the earplug with the desired functionality could be determined.

Several iterations were performed, wherein the sizes of the membranes and the meshes were modified with the aim to increase attenuation in the high attenuation mode and to reduce it in the low attenuation mode, specifically for the human speech range. An advantage is that the acoustic filter of the low attenuation mode allows the wearer to distinguish a human voice more clearly than without the acoustic filter, since much of the background noise is removed.

Figure 9:
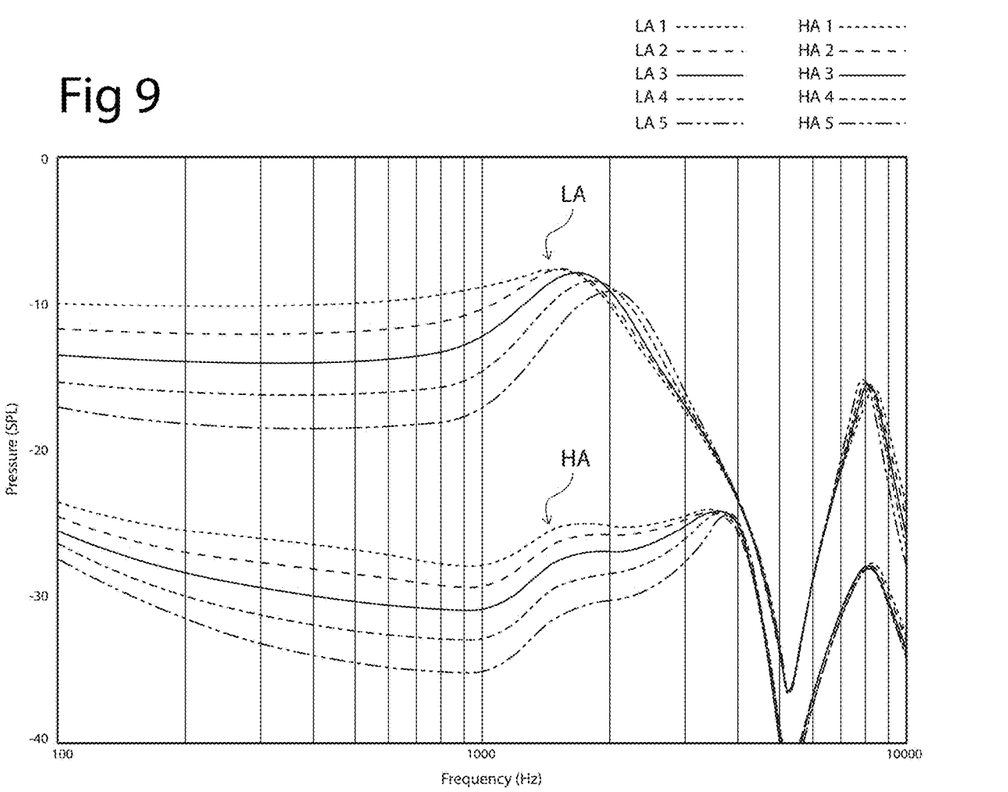
FIG. 9 is a diagram from acoustic simulations showing the insertion loss as a function of frequency and the sensitivity of the design of the ear plug.

FIG. 9 shows results from acoustic simulations showing the insertion loss as a function of frequency and the sensitivity of the design. Several iterations were performed, wherein the sizes of the membranes were modified with the aim to increase an average attenuation in the high attenuation mode (HA1, HA2, HA3, HA4, HA5) and reduce the average attenuation in the low attenuation mode (LA1, LA2, LA3, LA4, LA5) specifically for the human speech range.

A useful conclusion from the tests is that the control parameters 1 and 2 of each mesh and membrane, i.e. the open: surface area and the air permeability thereof, have greater impact on the attenuation than the other parameters. For example, when the diameter of the open surface area of the membranes is modified by 5%, a significant change in attenuation is achieved, which is illustrated in FIG. 9.

The body of the ear plug 10, 80 has several functions; it houses the insert 34 and the acoustic filters and keeps the tip 17 in place. The body is made of polycarbonate or a similar polymeric material, a metal or a ceramic material.

Figure 10:
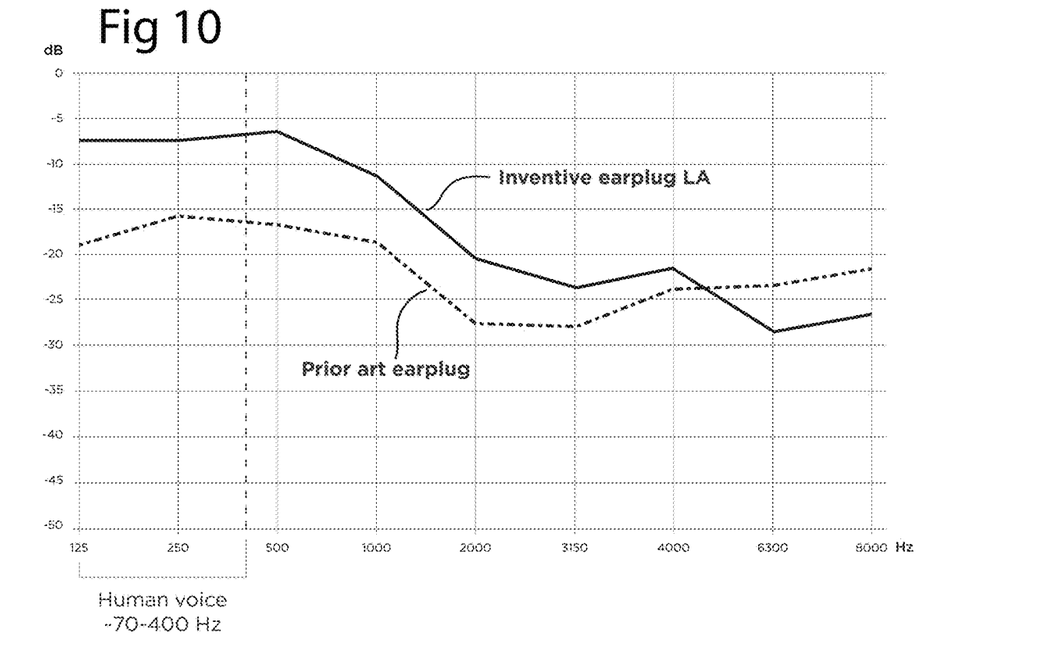
FIG. 10 is a diagram from acoustic laboratory tests showing the frequency response, meaning the attenuation as a function of frequency with the earplug in low attenuation mode in comparison with a prior art earplug made of silicone.

FIG. 10 is a diagram from acoustic laboratory tests showing the frequency response, meaning the attenuation as function of frequency, with the inventive earplug 10 in low attenuation mode in comparison with a prior art earplug made of silicone. The inventive earplug shows a lower degree of attenuation in the range of frequencies of the human voice, i.e. at 40-700 Hz, while higher frequencies are more attenuated. This improves a normal voice communication in noisy environments since frequencies outside the range of the human speech are filtered away in a determined extent.

Figure 11:
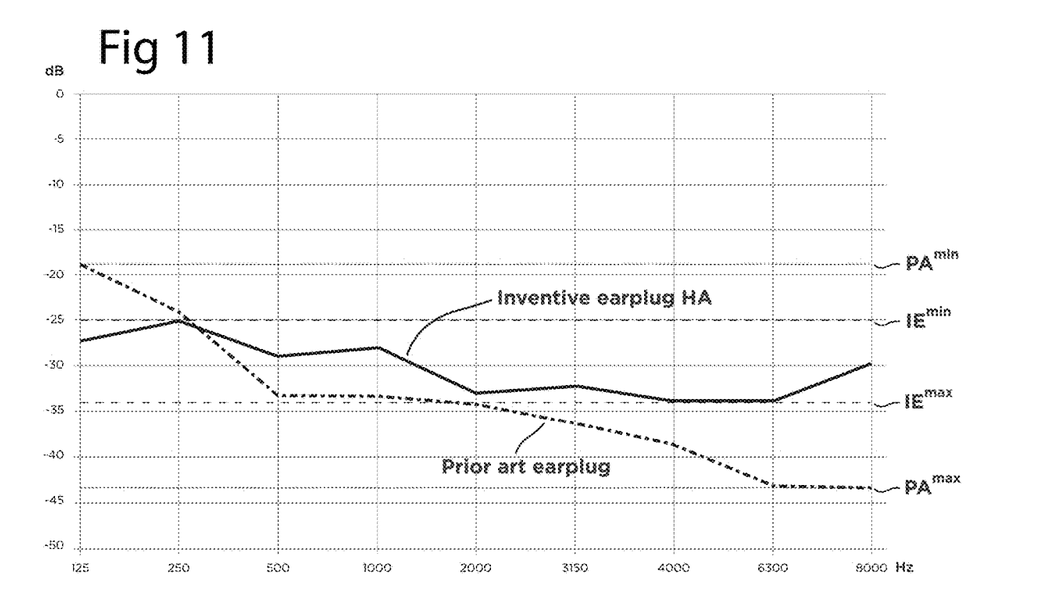
FIG. 11 is a diagram from acoustic laboratory tests showing the frequency response, meaning the attenuation as a function of frequency with the earplug in high attenuation mode in comparison with a prior art earplug made of foam.

FIG. 11 is a diagram from acoustic tests showing the frequency response, meaning attenuation as function of frequency, with the inventive earplug 10 in high attenuation mode in comparison with a prior art earplug made of foam.

As illustrated, a minimum attenuation $IE^{min}$ of the inventive earplug is about −25 dB, and a maximum attenuation $IE^{max}$ is about −34 dB in this iteration of the model. The prior art earplug made of silicone shows a larger range from a minimum attenuation $PA^{min}$ of about −18 dB to a maximum attenuation $PA^{max}$ of about −43 dB.

Further iterations, where some control parameters were slightly changed resulted in an average attenuation of about −30 dB across the entire frequency range for the inventive earplug. Hence a configuration of the earplug was found providing a clear listening experience without distortion and at a controlled reduced volume.

The highly modular design of the earplug enables to configure earplugs with varying acoustic features adapted for different use and environments. The repeated simulations and iterations of the control parameters, as described above, have shown that desired attenuation in a low and high mode can be provided, configured for high performing adjustable earplugs for different applications and environments.

The invention also relates to an insert 34 for use in an earplug 10, 80 or in an in-ear device with selective attenuation of frequencies of sound passing through said insert. Said insert 34 comprises at least one sound passage, where an acoustic filter is arranged. The acoustic filter comprises an upper acoustic port, at least one acoustic membrane and/or at least one acoustic mesh, an acoustic chamber and a lower acoustic port. Due to a determined configuration of the insert 34 a specific attenuation of sound passing said filter can be determined by a combination of a selected size of said upper and lower acoustic ports, a selected size of an open surface area of said at least one acoustic membrane and/or said at least one acoustic mesh, and a selected air permeability of said at least one acoustic membrane and/or said at least one acoustic mesh.

The insert 34 according to a first embodiment comprises a first sound passage with a first acoustic filter having a first upper acoustic port 45, a first acoustic mesh 35, a first acoustic chamber 41 and a first lower acoustic port 42, and comprises a second sound passage with a second acoustic filter having a second upper acoustic port 18, the first acoustic mesh 35, a first acoustic membrane 38, a second acoustic chamber 44, a second acoustic membrane 39 and a second acoustic lower port 43.

The insert 34 according to a second embodiment further comprises a third acoustic membrane.

The insert according to an alternative embodiment comprises one sound passage having an acoustic filter with determined frequency response and attenuation.

The acoustic membranes are made of a polymeric material, such as PTFE, and are configured as a thin porous film with an air permeability within the range of 4-150 L/m²s at a pressure of 200 Pa and with a DC flow resistance within the range of 2500-40 000 MKS Rayls.

The acoustic meshes are made of a polymeric material, such as polyester, and are configured as a woven mesh of monofilaments of said polymeric material with an air permeability within the range of 250-2500 L/m2s at a pressure of 200 Pa and a DC flow resistance within the range of 100-800 MKS Rayls.

A stiffness of said acoustic membranes and said acoustic meshes is a first parameter for determination of a specific frequency response of said acoustic filter and hence the attenuation, which is controlled by changing an open surface area of said acoustic membranes and said acoustic meshes.

A DC flow resistance of said acoustic membranes and said acoustic meshes is a second parameter for determination of a specific frequency response of said acoustic filter and hence the attenuation, which is controlled by changing an open surface area and said air permeability of said membranes and said acoustic meshes.

A third parameter for determination of a specific frequency response of said acoustic filter, and hence the attenuation, is controlled by changing a surface weight, a thickness and said open area of said acoustic membranes and said acoustic meshes.

A fourth parameter for determination of a specific frequency response of said acoustic filter, and hence the attenuation, is controlled by changing a volume and shape of said acoustic chambers.

A fifth parameter for determination of a specific frequency response of said acoustic filter, and hence the attenuation, is controlled by changing an open area of said acoustic ports.

With reference to the description of the ear plug 10, 80 in connection with FIG. 1-11, more features of said insert 34 will appear.

The earplugs 10, 80 according to the invention provide several advantages and benefits for a user compared to traditional earplugs.

The inventive earplug is specifically useful in situations such as workplaces with high noise levels for example industrial plants, where the user needs ear protection for extended periods, often entire working days, but also need to communicate with colleagues and stay alert of potential dangers of the environment. The inventive earplug enables the user to quickly switch between the high and low attenuation modes in real time without having to remove the earplug from the ear.

Also, the inventive earplug provides a better clarity in hearing compared to traditional earplugs. The low attenuation mode reduces background noise while preserving frequencies in the range of human speech, which in noisy environments enables the user to hear human speech more clearly compared to prior art earplugs, and more clearly compered to wearing no earplugs at all since the reduction of background noise makes human speech more easily distinguishable.

When the inventive earplugs are used at loud events like music concerts, in bars and night clubs the wearer gets the benefit of staying protected while being able to enjoy a clearer listening experience due to the very flat frequency response of the high attenuation mode, providing minimal distortion to the sound coming through to the ear. The user can easily switch to the low attenuation mode when communicating with people and still maintain a good hearing protection.

Whether a user of the earplugs visits concerts frequently, or is a musician, a sound technician or a kindergarten teacher, the earplugs will protect the ears with minimal impact on sound quality. If the wearer works in an open office environment, reads or studies, the earplugs will attenuate surrounding sound and help to focus.

A leash attached by its ends to the bodies of the pair of earplugs allows the wearer to keep the earplugs snapped around the neck due to the magnets of the sliding members, which will always keep the earplugs available for use.

Since the ear plugs are light, smooth and sleek, these are also suitable for sleeping. The ear plug is a purely mechanical product without any electronics or batteries, thus no charging is needed.

The description above shall be considered as an exemplification of the principles of the invention and are not intended to limit the invention to the specific embodiments as illustrated. Other embodiments than the ones described can exist within the scope of protection, for example an alternative embodiment of the ear plug can have a different design of the insert to arrange an additional mesh and/or membrane to attenuate other selected frequencies. Also, the sizes of said meshes and/or membranes could be changed and/or air chambers could be modified to comply with attenuation of other selected frequencies, since it has been shown that the five control parameters in combination are essential for the configuration of the earplug to reach a specific level of attenuation and hence frequency response.

Alternative embodiments of the inventive earplug could be provided having three passages, which each comprises an acoustic filter. Also, developments of the ear plug may omit the insert, and in such case the membranes and the meshes are arranged to the inner surfaces of the body by adhesives.

Also, the means 14 at the top surface 12 of the body 11 can be configured differently than the sliding member 14 for activating a sound passage in use.

It should be emphasized that the term "comprise/comprising" when used in this specification is taken to specify the presence of stated features, integers, steps, or components, but does not exclude the presence or additions of one or more other features, other elements or steps. Reference signs in the claims are provided as clarifying examples and shall not be construed as limiting the scope in any way.

The invention claimed is:

1. A pair of earplugs, each earplug for selective attenuation of sound from the environment reaching a respective inner ear of a user, each earplug comprising a body having a first sound path and a second sound path extending through the body, each earplug further comprising:
    a top wall of the body with a first inlet facing ambient air of the environment and a second inlet facing the ambient air of the environment, the first inlet opening to the first sound path and the second inlet opening to the second sound path,
    an acoustic filter arranged in each of the sound paths, each acoustic filter having a different attenuation of sound passing the acoustic filter,
    a cover attached to the body and slidable with respect to the top wall between a first position that covers the first inlet and exposes the second inlet to the ambient air so as to activate the second sound path and deactivate the first sound path, and a second position that covers the second inlet and exposes the first inlet to the ambient air so as to activate the first sound path and deactivate the second sound path, and
    a magnet retained by the earplug and positioned to magnetically connect the earplugs of the pair to each other, and
    wherein each earplug further comprises an insert located in the body and having the acoustic filters of the sound paths,
    wherein, for each earplug, the insert has a first passage forming an acoustic chamber of the first acoustic filter and a second passage forming an acoustic chamber of the second acoustic filter, and
    wherein, for each earplug, the first and the second acoustic filters comprise an acoustic mesh or an acoustic membrane that covers both the first passage of the insert and the second passage of the insert.

2. The pair of earplugs according to claim 1, wherein, for each earplug, the body comprises a side wall protruding toward the environment from the top wall, the side wall comprising opposing and inwardly protruding ridges that engage and hold the cover from separating from the body.

3. The pair of earplugs according to claim 1, wherein, for each earplug, the first acoustic filter comprises:

a first upper acoustic port, and
a first lower acoustic port, and
the second acoustic filter comprises:
a second upper acoustic port,
another acoustic mesh or acoustic membrane different than the acoustic mesh or acoustic membrane that covers both the first passage of the insert and the second passage of the insert, and
a second lower acoustic port.

4. The pair of earplugs according to claim 1, wherein, for each earplug, each acoustic filter comprises:
an upper acoustic port, and
a lower acoustic port, and
wherein a specific attenuation of sound passing the acoustic filter is determined by a combination of a selected size of an open area of the upper and lower acoustic ports and a selected size of an open surface area of the acoustic membrane or acoustic mesh, and a selected air permeability of the acoustic membrane or acoustic mesh.

5. The pair of earplugs according to claim 4, wherein, for each earplug, the acoustic mesh or membrane is an acoustic membrane made of a polymeric material configured as a thin porous film with an air permeability within the range of 4-150 L/m$^2$s at a pressure of 200 Pa and with a DC flow resistance within the range of 2500-40 000 MKS Rayls.

6. The pair of earplugs according to claim 4, wherein, for each earplug, the acoustic mesh or membrane is an acoustic mesh made of a polymeric material configured as a woven mesh of monofilaments of said polymeric material with an air permeability within the range of 250-2500 L/m$^2$s at a pressure of 200 Pa and a DC flow resistance within the range of 100-800 MKS Rayls.

7. The pair of earplugs according to claim 1, wherein, for each earplug, the magnet of each earplug is located in the cover of the earplug.

8. A pair of earplugs, each earplug for selective attenuation of sound from the environment reaching a respective inner ear of a user, each earplug comprising a body having a first sound path and a second sound path extending through the body, each earplug further comprising:
a top wall of the body with a first inlet facing ambient air of the environment and a second inlet facing the ambient air of the environment, the first inlet opening to the first sound path and the second inlet opening to the second sound path,
an acoustic filter arranged in each of the sound paths, each acoustic filter having a different attenuation of sound passing the acoustic filter,
a cover attached to the body and slidable with respect to the top wall between a first position that covers the first inlet and exposes the second inlet to the ambient air so as to activate the second sound path and deactivate the first sound path, and a second position that covers the second inlet and exposes the first inlet to the ambient air so as to activate the first sound path and deactivate the second sound path, and
a magnet retained by the earplug and positioned to magnetically connect the earplugs of the pair to each other, and
wherein, for each earplug, the cover comprises a disc retained by the body and a silicone rubber seal that forms an airtight seal over the covered one of the inlets.

9. An earplug, comprising:
a body having a hollow interior comprising:
a tubular portion configured for insertion into an ear of a user and surrounding a through bore portion of the hollow interior that extends from an output opening of the earplug at a lower end of the tubular portion to an upper end of the tubular portion, and
an upper body portion having a primary wall facing away from the user, the primary wall having a first opening forming a first inlet port into the hollow interior and a second opening distinct from the first opening, the second opening forming a second inlet port into the hollow interior, and the upper body portion surrounding a first acoustic pathway extending from the first inlet port to the through bore at the upper end of the tubular portion and a second acoustic pathway distinct from the first acoustic pathway extending from the second inlet port to the through bore at the upper end of the tubular portion;
a first acoustic membrane or mesh that covers both the first opening and the second opening;
a second acoustic membrane or mesh that traverses the first acoustic pathway between the first acoustic membrane or mesh and the through bore such that attenuation of sound by the first acoustic pathway is different from attenuation of sound by the second acoustic pathway; and
a cover attached to the body and slidable with respect to the primary wall between a first position in which the cover forms a seal over the first opening and exposes the second opening to ambient air and a second position in which the cover forms a seal over the second opening and exposes the first opening to the ambient air so as to selectively activate the attenuation of one of the first acoustic pathway or the second acoustic pathway at a time.

10. The earplug according to claim 9, further comprising a third acoustic membrane or mesh that traverses the first acoustic pathway between the first acoustic membrane or mesh and the second acoustic membrane or mesh.

11. The earplug according to claim 10, wherein the third acoustic membrane or mesh divides an acoustic chamber in the first acoustic pathway.

12. The earplug according to claim 9, further comprising an insert having a first passage forming an acoustic chamber of the first acoustic pathway and a second passage forming an acoustic chamber of the second acoustic pathway.

13. The earplug according to claim 12, wherein the first acoustic membrane or mesh is secured to an inner surface of the primary wall.

14. The earplug according to claim 13, wherein the first acoustic membrane or mesh is secured to the inner surface of the primary wall with first layer of adhesive and is secured to the insert with a second layer of adhesive.

15. The earplug according to claim 14, wherein the first and second layers of adhesive form an airtight seal between the primary wall and the hollow interior of the body.

16. The earplug according to claim 9, wherein the cover comprises a disc retained by the body and a silicone rubber seal that forms an airtight seal over the covered one of the inlets.

* * * * *